(12) United States Patent
Castelli et al.

(10) Patent No.: US 7,378,553 B2
(45) Date of Patent: May 27, 2008

(54) ISOLATED ATOMOXETINE IMPURITY, PROCESSES FOR THE PREPARATION OF ATOMOXETINE IMPURITIES AND THEIR USE AS REFERENCE STANDARDS

(75) Inventors: Eugenio Castelli, Arlate di Calco (IT); Alessandra Vailati, Seregno (IT)

(73) Assignee: Teva Pharmaceutical Fine Chemicals S.r.l., Bulciago (LC) (IT)

( * ) Notice: Subject to any disclaimer, the term of this patent is extended or adjusted under 35 U.S.C. 154(b) by 202 days.

(21) Appl. No.: 11/170,430

(22) Filed: Jun. 28, 2005

(65) Prior Publication Data

US 2006/0009532 A1  Jan. 12, 2006

Related U.S. Application Data

(60) Provisional application No. 60/690,738, filed on Jun. 14, 2005, provisional application No. 60/689,778, filed on Jun. 9, 2005, provisional application No. 60/675,369, filed on Apr. 26, 2005, provisional application No. 60/666,666, filed on Mar. 30, 2005, provisional application No. 60/652,331, filed on Feb. 11, 2005, provisional application No. 60/652,330, filed on Feb. 11, 2005, provisional application No. 60/652,332, filed on Feb. 11, 2005, provisional application No. 60/622,065, filed on Oct. 25, 2004, provisional application No. 60/609,716, filed on Sep. 14, 2004, provisional application No. 60/583,644, filed on Jun. 28, 2004, provisional application No. 60/583,643, filed on Jun. 28, 2004, provisional application No. 60/583,641, filed on Jun. 28, 2004.

(51) Int. Cl.
*C07C 213/06* (2006.01)
(52) U.S. Cl. ..................................... 564/355
(58) Field of Classification Search ...................... None
See application file for complete search history.

(56) References Cited

U.S. PATENT DOCUMENTS

| 4,018,895 | A | 4/1977 | Molloy et al. |
| 4,777,291 | A | 10/1988 | Misner |
| 4,868,344 | A | 9/1989 | Brown |
| 5,658,590 | A | 8/1997 | Heiligenstein et al. |
| 6,333,198 | B1 | 12/2001 | Edmeades et al. |
| 6,541,668 | B1 | 4/2003 | Kjell et al. |

FOREIGN PATENT DOCUMENTS

| DE | 41 23 253 A1 | 1/1993 |
| EP | 0 052 492 A1 | 5/1982 |
| EP | 0 193 405 A1 | 9/1986 |
| EP | 0 721 777 A2 | 1/1995 |
| WO | WO 94/00416 | 1/1994 |
| WO | WO 00/58262 | 10/2000 |
| WO | WO 00/64855 | 11/2000 |
| WO | WO 2006/004923 A2 | 1/2006 |
| WO | WO 2006/004976 A2 | 1/2006 |
| WO | WO 2006/004977 A2 | 1/2006 |
| WO | WO 2006/020348 A2 | 2/2006 |
| WO | WO 2006/068662 A1 | 6/2006 |

OTHER PUBLICATIONS

Database CAPLUS on STN, Acc. No. 2001:636023, Cheshire et al., WO 2001062704 (Aug. 30, 2001) (abstract).*
Database CAPLUS on STN, Acc. No. 1992:489890, Wheeler, Journal of Labelled Compounds and Radiopharmaceuticals (1992), 31(6), p. 477-87 (abstract).*
Database CASREACT on STN, No. 117:89890, Wheeler, Journal of Labelled Compounds and Radiopharmaceuticals (1992), 31(6), p. 477-87 (reaction abstract).*
O'Brien et al., Tetrahedron Letters (2002), 43(41), p. 7333-7335.*
Database CAPLUS on STN, Acc. No. 1995:449521, Lacroix et al., Journal of AOAC International (1995), 78(2), p. 334-339 (abstract).*
Database CAPLUS on STN, Acc. No. 1998:26204, Wirth et al., Chromatographia (1997), 49(9/10), p. 511-523 (abstract).*
Srebnik, M. et al. "Chiral Synthesis via Organoboranes. 18. Selective Reductions. 43. Dissopinocampheylchloroborane as an Excellent . . . " J. Org. Chem. (1988), vol. 53, p. 2916-2920.
Anon (R)-(-)-N-Methyl-3-(2-Methylphenoxy)Phenyl-3-Phenylpropylamine (S)-(+)-Mandelate Chemical Abstracts Service XP-002367856 Dec. 29, 2004.
Koenig, T.M. et al. "A Convenient Method for Preparing Enantiomerically Pure Norfluoxetine, Fluoxetine and Tomoxetine" Tetrahedron Letters, vol. 35, No. 9, pp. 1339-1342 (1994).
Strobel, H.A.; Heineman, W.R., Chemical Instrumentation: A Systematic Approach, 3rd dd. (Wiley & Sons: New York 1989)—pp. 391-393, 879-894, 922-925, 953.
Snyder, L.R.; Kirkland, J.J., Introduction to Modern Liquid Chromatography, 2nd ed. (John Wiley & Sons: New York 1979)—p. 549-552, 571-572.
Sellers, J.A. et al. "Determination of the Enantiomer and Positional Isomer Impurities in Atomoxetine Hydrochloride with Liquid Chromatography Using Polysaccharide Chiral Stationary Phases." *J. of Pharmaceutical and Biomedical Analysis*, vol. 41, pp. 1088-1094 (2006).

* cited by examiner

Primary Examiner—Brian Davis
(74) Attorney, Agent, or Firm—Kenyon & Kenyon LLP

(57) ABSTRACT

The present invention provides isolated N-methyl-3-(3-methylphenoxy)-3-phenylpropylamine hydrochloride, and preparation thereof as well as of N-methyl-3-(4-methylphenoxy)-3-phenylpropylamine hydrochloride and of N-methyl-3-phenoxy-3-phenylpropylamine hydrochloride. The invention further provides the use of the above compounds as reference markers and/or reference standards during the synthesis of Atomoxetine. Also provided is a method of limiting the amounts of the impurities 3FT (3-fluorotoluene), 4FT (4-fluorotoluene), and FB (fluorobenzene) in the 2-fluorotoluene starting material used in the synthesis of Atomoxetine Hydrochloride. The purity of the Atomoxetine Hydrochloride product is ensured by determining the amounts of 3FT, 4FT, and FB in the 2-fluorotoluene starting material with the marker 3-ATM HCl.

19 Claims, 4 Drawing Sheets

ISOLATED ATOMOXETINE IMPURITY, PROCESSES FOR THE PREPARATION OF ATOMOXETINE IMPURITIES AND THEIR USE AS REFERENCE STANDARDS

CROSS-REFERENCE TO RELATED APPLICATIONS

This application claims the benefits of U.S. Provisional Patent Application Ser. Nos. 60/583,641, filed Jun. 28, 2004, 60/609,716, filed Sep. 14, 2004, 60/622,065, filed Oct. 25, 2004, 60/652,330, filed Feb. 11, 2005, 60/583,644, filed Jun. 28, 2004, 60/652,332, filed Feb. 11, 2005, 60/583,643, filed Jun. 28, 2004, 60/652,331, filed Feb. 11, 2005, 60/666,666, filed Mar. 30, 2005, 60/675,369, filed Apr. 26, 2005, 60/689, 778, filed Jun. 9, 2005, and 60/690,738, filed Jun. 14, 2005, the contents of all of which are incorporated herein by reference.

FIELD OF THE INVENTION

The present invention relates to an isolated impurity of Atomoxetine hydrochloride, its preparation as well as the preparation of other impurities, and their use as reference standards.

BACKGROUND OF THE INVENTION

Atomoxetine (ATM), known as (R)(−)-N-methyl-3-(2-methylphenoxy)-3-phenylpropylamine, has the following structure:

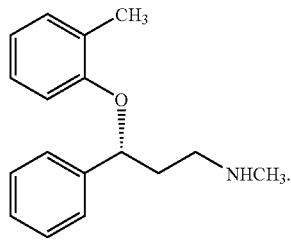

In addition, Atomoxetine has the formula $C_{17}H_{21}NO$, a molecular weight of 255.35, and a composition of 79.96 percent C, 8.29 percent H, 5.49 percent N, and 6.27 percent O, by weight. The hydrogen chloride salt of Atomoxetine, Atomoxetine HCl, is marketed as STRATTERA®, which is prescribed as oral capsules having dosages of 10 mg, 18 mg, 25 mg, 40 mg, and 60 mg for the treatment of Attention-Deficit-Hyperactivity Disorder (ADHD). Atomoxetine is a competitive inhibitor of norepinephrine uptake in synaptosomes of rat hypothalamus, 2 and 9 times more effective than the racemic mixture and the (+)-enantiomer, respectively, of N-methyl-3-(2-methylphenoxy)-3-phenylpropylamine (Tomoxetine, "TMX"), disclosed in EP 0 052 492. Atomoxetine is the (R)-(−) enantiomer of Tomoxetine.

Racemic Tomoxetine as well as many other aryloxyphenylpropylamines, e.g., FLUOXETINE® and NISOXETINE®, are disclosed in U.S. Pat. No. 4,018,895, which also discloses a psychotropic effect of the compounds. Atomoxetine, including its pharmaceutically acceptable addition salts, e.g., the hydrochloride, is disclosed in EP 0 052 492, which also discloses their use as antidepressants. The use of atomoxetine in the treatment of ADHD was disclosed in EP 0 721 777.

Manufacturing processes for Atomoxetine Hydrochloride, known in the art, include those disclosed in European Patent Publication No. EP 0 052 492, U.S. Pat. Nos. 4,868,344 and 6,541,668, International Patent Application Publication No. WO 00/58262, the teachings of which are incorporated herein by reference.

It is well known in the art that, for human administration, safety considerations require the establishment, by national and international regulatory authorities, of very low limits for identified, but toxicologically uncharacterized impurities, before an active pharmaceutical ingredient (API) product is commercialized. Typically, these limits are less than about 0.15 percent by weight of each impurity. Limits for unidentified and/or uncharacterized impurities are obviously lower, typically, less than 0.1 percent by weight. Therefore, in the manufacture of APIs, the purity of the products, such as Atomoxetine Hydrochloride, is required before commercialization, as is the purity of the active agent in the manufacture of formulated pharmaceuticals.

It is also known in the art that impurities in an API may arise from degradation of the API itself, which is related to the stability of the pure API during storage, and the manufacturing process, including the chemical synthesis. Process impurities include unreacted starting materials, chemical derivatives of impurities contained in starting materials, synthetic by-products, and degradation products.

In addition to stability, which is a factor in the shelf life of the API, the purity of the API produced in the commercial manufacturing process is clearly a necessary condition for commercialization. Impurities introduced during commercial manufacturing processes must be limited to very small amounts, and are preferably substantially absent. For example, the ICH Q7A guidance for API manufacturers requires that process impurities be maintained below set limits by specifying the quality of raw materials, controlling process parameters, such as temperature, pressure, time, and stoichiometric ratios, and including purification steps, such as crystallization, distillation, and liquid-liquid extraction, in the manufacturing process.

The product mixture of a reaction is rarely a single compound with sufficient purity to comply with pharmaceutical standards. Side products and by-products of the reaction and adjunct reagents used in the reaction will, in most cases, also be present in the product mixture. At certain stages during processing of an API, such as Atomoxetine Hydrochloride, it must be analyzed for purity, typically, by HPLC or GC analysis, to determine if it is suitable for continued processing and, ultimately, for use in a pharmaceutical product. The API need not be absolutely pure, as absolute purity is a theoretical ideal that is typically unattainable. Rather, purity standards are set with the intention of ensuring that an API is as free of impurities as possible, and, thus, is as safe as possible for clinical use. As discussed above, in the United States, the Food and Drug Administration guidelines recommend that the amounts of some impurities be limited to less than 0.1 percent.

Generally, side products, by-products, and adjunct reagents (collectively "impurities") are identified spectroscopically and/or with another physical method, and then associated with a peak position, such as that in a chromatogram, or a spot on a TLC plate. (Strobel p. 953, Strobel, H. A.; Heineman, W. R., Chemical Instrumentation: A Systematic Approach, 3rd dd. (Wiley & Sons: New York 1989)). Thereafter, the impurity can be identified, e.g., by its relative position in the chromatogram, where the position in a chromatogram is conventionally measured in minutes between injection of the sample on the column and elution of the particular component through the detector. The relative position in the chromatogram is known as the "retention time." The retention time varies daily, or even over the course of a day, based upon the condition of the instrumentation, as well as many other factors. To mitigate the effects such variations have upon accurate identification of an impurity, practitioners use the "relative retention time" ("RRT") to identify impurities. (Strobel p. 922). The RRT of an impurity is its retention time divided by the retention time of a reference marker. In theory, Atomoxetine Hydrochloride itself could be used as the reference marker, but as a practical matter it is present in such a large proportion in the mixture that it can saturate the column, leading to irreproducible retention times, as the maximum of the peak can wander (Strobel, FIG. 24.8(b), p. 879, illustrates an asymmetric peak observed when a column is overloaded). Thus, it may be advantageous to select a compound other than the API that is added to, or present in, the mixture in an amount sufficiently large to be detectable and sufficiently low as not to saturate the column, and to use that compound as the reference marker.

Those skilled in the art of drug manufacturing research and development understand that a compound in a relatively pure state can be used as a "reference standard." A reference standard is similar to a reference marker, which is used for qualitative analysis only, but is used to quantify the amount of the compound of the reference standard in an unknown mixture, as well. A reference standard is an "external standard," when a solution of a known concentration of the reference standard and an unknown mixture are analyzed using the same technique. (Strobel p. 924, Snyder p. 549, Snyder, L. R.; Kirkland, J. J. Introduction to Modern Liquid Chromatography, 2nd ed. (John Wiley & Sons: New York 1979)). The amount of the compound in the mixture can be determined by comparing the magnitude of the detector response. See also U.S. Pat. No. 6,333,198, incorporated herein by reference.

The reference standard can also be used to quantify the amount of another compound in the mixture if a "response factor," which compensates for differences in the sensitivity of the detector to the two compounds, has been predetermined. (Strobel p. 894). For this purpose, the reference standard is added directly to the mixture, and is known as an "internal standard." (Strobel p. 925, Snyder p. 552).

The reference standard can even be used as an internal standard when, without the addition of the reference standard, an unknown mixture contains a detectable amount of the reference standard compound using a technique known as "standard addition." In a "standard addition," at least two samples are prepared by adding known and differing amounts of the internal standard. (Strobel pp. 391-393, Snyder pp. 571, 572). The proportion of the detector response due to the reference standard present in the mixture without the addition can be determined by plotting the detector response against the amount of the reference standard added to each of the samples, and extrapolating the plot to zero. (See, e.g., Strobel, FIG. 11.4 p. 392).

As is known by those skilled in the art, the management of process impurities is greatly enhanced by understanding their chemical structures and synthetic pathways, and by identifying the parameters that influence the amount of impurities in the final product.

SUMMARY OF THE INVENTION

Figure 1:
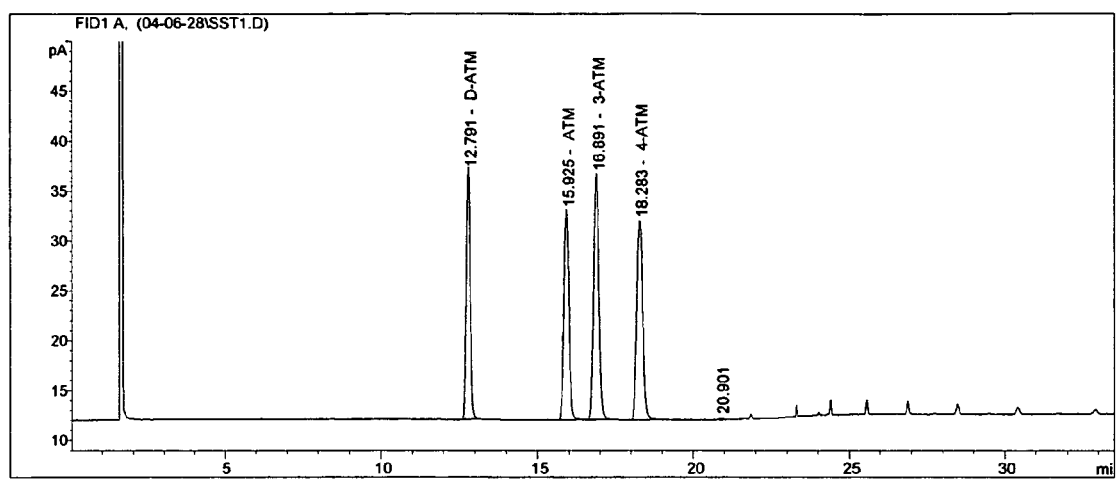
FIG. 1 shows a typical chromatogram of ATM-HCl impurities obtained via GC on a HP-35: 35% Phenyl Methyl Siloxane (Hewlett Packard cat. No 19091G-113) column.

In the first embodiment, this invention is directed to an isolated Atomoxetine HCl impurity; the isolated hydrochloride salt of N-methyl-3-(3-methylphenoxy)-3-phenylpropylamine (3-ATM HCl).

In another embodiment, this invention is directed to methods for preparing 3-ATM HCl, by reacting 3-fluorotoluene (3FT) with the alkolate of N-methyl-3-hydroxy-3-phenylpropylamine, under the process conditions defined below.

In yet another embodiment, this invention is directed to methods of preparing N-methyl-3-(4-methylphenoxy)-3-phenylpropylamine (4-ATM HCl), another Atomoxetine HCl impurity, by reacting 4-fluorotoluene (4FT) with the alkolate of N-methyl-3-hydroxy-3-phenylpropylamine, under the process conditions defined below.

In yet another embodiment, this invention is directed to methods of preparing N-methyl-3-phenoxy-3-phenylpropylamine (D-ATM HCl), yet another Atomoxetine HCl impurity, by reacting fluorobenzene (FB) with the alkolate of N-methyl-3-hydroxy-3-phenylpropylamine, under the process conditions defined below.

In one embodiment, the invention is directed to the use of 3-ATM HCl, as well as of the two Atomoxetine HCl impurities, 4-ATM HCl and D-ATM HCl as reference markers in a qualitative analysis of Atomoxetine HCl.

In another embodiment, the invention is directed to a method of using 3-ATM HCl, 4-ATM HCl and D-ATM HCl as reference standards to analytically quantify the purity of Atomoxetine Hydrochloride.

In yet another embodiment, the invention is directed to a method to define the limits for the amounts of 3FT, 4FT, and FB impurities in the 2FT starting material for the synthesis of Atomoxetine Hydrochloride of a desired purity, comprising the use of 3-ATM HCl, 4-ATM HCl and D-ATM HCl as reference standards.

In a further embodiment, the invention is directed to a method for the quantification of the purity of Atomoxetine Hydrochloride, comprising the use of 3-ATM HCl, 4-ATM HCl and D-ATM HCl as reference standards, where the reference standards may be either external standards or internal standards.

In one embodiment, the invention is directed to an analytical method for the analysis of the purity of 2-fluorotoluene.

In another embodiment, the invention is directed to a method comprising limiting the amounts of the impurities 3FT, 4FT, and FB in the 2FT starting material used in the synthesis of Atomoxetine Hydrochloride to ensure the purity of the Atomoxetine Hydrochloride product by determining the amounts of 3FT, 4FT, and FB in the 2-fluorotoluene starting material, using at least one of 3-ATM HCl, 4-ATM HCl and D-ATM HCl as a reference standard.

In yet another embodiment, the invention is directed to a novel GC method, used for the measuring of the three impurities in an atomoxetine HCl sample. In a further embodiment, the invention is directed to a novel GC method, used for the measuring of 3FT, 4FT and FB in a 2-fluorotoluene sample.

DESCRIPTION OF THE INVENTION

As used herein, unless the context requires otherwise, the three impurities referred to in the application include both the racemic mixture and the enantiomerically pure forms. Thus, for example, N-methyl-3-(3-methylphenoxy)-3-phenylpropylamine (and its acronym "3-ATM HCl") refers to either (±)-N-methyl-3-(3-methylphenoxy)-3-phenylpropylamine or (R)(−)-N-methyl-3-(3-methylphenoxy)-3-phenylpropylamine.

As used herein the term "aromatic solvent" refers to a $C_{6-10}$ aromatic hydrocarbon such as, but not limited to, benzene, xylene, or toluene.

As used herein, the term "predetermined level", in reference to the level of the impurities 3-ATM HCl, 4-ATM HCl and D-ATM HCl, means a level of 0.15% or less, as measured by GC or HPLC.

As used herein, the term "isolated" refers to a compound that is at least 80%, preferably at least 90%, even more preferably at least5 95%, and most preferably at least 99% pure, as judged by GC or HPLC.

A "reference marker" is used in qualitative analysis to identify components of a mixture based upon their position, e.g., in a chromatogram or on a Thin Layer Chromatography (TLC) plate (Strobel pp. 921, 922, 953). For this purpose, the compound does not necessarily have to be added to the mixture if it is present in the mixture. A "reference marker" is used only for qualitative analysis, while a reference standard may be used for quantitative or qualitative analysis, or both. Hence, a reference marker is a subset of a reference standard, and is included within the definition of a reference standard.

As used herein, the term "reference standard" refers to a compound that may be used both for quantitative and qualitative analysis of an active pharmaceutical ingredient. For example, the HPLC or GC retention time of the compound allows a relative retention time to be determined, thus making qualitative analysis possible. The concentration of the compound in solution before injection into an HPLC or GC column allows the areas under the HPLC or GC peaks to be compared, thus making quantitative analysis possible.

Reference standards are described in general terms above. However, as will be understood by those skilled in the art, a detector response can be, for example, the peak heights or integrated peak areas of a chromatogram obtained, e.g., by UV or refractive index detection, from the eluent of an HPLC system or, e.g., flame ionization detection (FID) or thermal conductivity detection, from the eluent of a gas chromatograph, or other detector response, e.g., the UV absorbance of spots on a fluorescent TLC plate. The position of the reference standard may be used to calculate the relative retention time for Atomoxetine Hydrochloride and impurities of Atomoxetine Hydrochloride.

As used herein, the term "substantially", in reference to RRTs being substantially the same, refers to a relative standard deviation that is equal to or less than 5% for a population of 6 injections.

The present invention is directed to an impurity of Atomoxetine Hydrochloride, which was previously unidentified, its preparation as well as of other known impurities, and to the use of these impurities as reference standards for the analytical quantification of Atomoxetine Hydrochloride purity, as required in the manufacture of high purity Atomoxetine Hydrochloride.

Three hydrochloride impurities have been identified in the (±)Tomoxetine solutions and the final product. The three hydrochloride impurities are N-methyl-3-(3-methylphenoxy)-3-phenylpropylamine (3-ATM HCl), a previously unidentified compound, as well as the hydrochloride salt of N-methyl-3-(4-methylphenoxy)-3-phenylpropylamine (4-ATM HCl), and the hydrochloride salt of N-methyl-3-phenoxy-3-phenylpropylamine (D-ATM HCl). These three hydrochloride impurities are formed by reacting 3-fluorotoluene (3FT), 4-fluorotoluene (4FT), and fluorobenzene (FB), respectively, with the alkolate of N-methyl-3-hydroxy-3-phenylpropylamine. The hydrochloride impurities have been found to be surprisingly difficult to remove using normal purification steps.

The present invention provides an isolated Atomoxetine Hydrochloride impurity, N-methyl-3-(3-methylphenoxy)-3-phenylpropylamine (3-ATM HCl), having the structure:

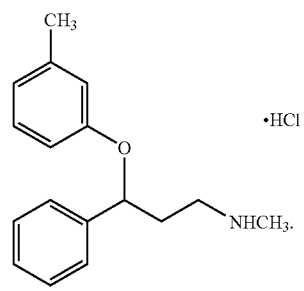

The 3-ATM HCl impurity is a regio-isomer of Atomoxetine.

The present invention provides a process for the preparation of 3-ATM HCl by reaction of 3-fluorotoluene, an impurity of 2-fluorotoluene, with the alkolate of N-methyl-3-hydroxy-3-phenylpropylamine. This process comprises:
  a) combining N-methyl-3-hydroxy-3-phenylpropylamine with DMSO in the presence of a strong base at a temperature of at least 90° C.;
  b) adding 3-fluorotoluene and maintaining the reaction mixture for at least 5 hours;
  c) adding a first organic solvent and water to the reaction mixture;
  d) recovering crude (±)3-methyl Tomoxetine base;
  e) combining crude (±)3-methyl Tomoxetine base with (S)-(+)-Mandelic acid in the presence of a $C_{1-4}$ alcohol and an aromatic solvent, and heating to a temperature of about 65° C. to about 70° C.;
  f) recovering 3-methyl Atomoxetine (S)-(+)-Mandelate salt;
  g) combining 3-methyl Atomoxetine (S)-(+)-Mandelate salt with a second organic solvent, water and a base;
  h) recovering 3-methyl Atomoxetine base;
  i) converting the 3-methyl Atomoxetine base to the corresponding hydrochloride salt.

DMSO in step a) may be added in a relatively small amount, and may even be considered a catalyst. Preferably, the amount of DMSO is about 0.1 to about 20 moles per moles of N-methyl-3-hydroxy-3-phenylpropylamine. Most preferably, the amount of DMSO is about 3 to about 4 moles per moles of N-methyl-3-hydroxy-3-phenylpropylamine.

The strong base in step a) may be any one of NaOH, KOH, Ca(OH)$_2$ or Ba(OH)$_2$. Preferably, the strong base is KOH. The base is preferably present in an amount of about 3 to about 4 moles per moles of moles of N-methyl-3-hydroxy-3-phenylpropylamine.

The 3-fluorotoluene added in step b) is preferably at an amount of at least 2 moles per moles of N-methyl-3-hydroxy-3-phenylpropylamine.

Preferably, the first organic solvent in step c) is selected from the group consisting of C$_{5-10}$ aliphatic and aromatic hydrocarbons, which aromatic hydrocarbons may be substituted with one or more (preferably one to three) C$_{1-3}$ alkyl groups, C$_{3-8}$ alkyl esters and C$_{3-8}$ alkyl ethers. More preferably, the organic solvent is selected from the group consisting of toluene, benzene, xylenes, di-isopropyl ether, methyl-tert-butyl, ethyl acetate n-butylacetate, and isobutylacetate. Most preferably, the organic solvent is toluene.

Preferably, the C$_{1-4}$ alcohol in step e) is added in an amount of about 0.1 mL per 1 g of the (±)3-methyl Tomoxetine base. Most preferably, the C$_{1-4}$ alcohol is methanol. The aromatic solvent can be an aromatic hydrocarbon which may be substituted with one or more (preferably one to three) C$_{1-10}$ alkyl groups, such as toluene, benzene, xylenes. A preferred aromatic solvent is toluene. Preferably, following heating, the reaction mixture is cooled to a temperature of about 0° C. to about 20° C. Preferably, the reaction mixture is cooled to a temperature of about 5° to about 10°.

Preferably, the base in step g) is selected from an alkali metal hydroxide, such as NaOH or KOH, or an alkali metal carbonate such as Na$_2$CO$_3$ or K$_2$CO$_3$. Most preferably, the base is NaOH Preferably the second organic solvent in step g) is selected from the group consisting of aliphatic or aromatic hydrocarbons such as C$_{5-8}$ alkanes, toluene and xylene, C$_{1-4}$ alkyl esters such as methyl acetate, ethyl acetate, n-butyl acetate and iso-butyl acetate, ketones such as methyl-ethyl ketone, linear or branched C$_{4-8}$ alcohols such as n-butanol, 2-butanol and n-pentanol and mixtures thereof. More preferably, the second organic solvent is selected from the group consisting of ethyl acetate, n-butyl acetate and iso-butyl acetate. Most preferably, the second organic solvent is n-butyl acetate.

The second impurity is N-methyl-3-(4-methylphenoxy)-3-phenylpropylamine (4-ATM), is disclosed in U.S. Pat. No. 4,018,895, and has the structure:

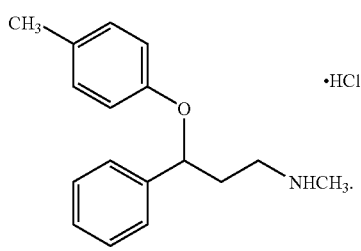

The 4-ATM compound is a regio-isomer of Atomoxetine.

The present invention provides a process for its preparation by reaction of 4-fluorotoluene, an impurity of 2-fluorotoluene, with the alkolate of N-methyl-3-hydroxy-3-phenylpropylamine, under the process conditions described above for the preparation of 3-ATM HCl.

The third impurity is N-methyl-3-phenoxy-3-phenylpropylamine or "Des-methyl Atomoxetine" (D-ATM). This compound is disclosed in U.S. Pat. No. 4,018,895, and has the structure:

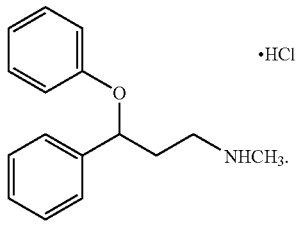

The present invention provides a process for the preparation of the D-ATM impurity by reaction of fluorobenzene, an impurity of 2-fluorotoluene, with the alkolate of N-methyl-3-hydroxy-3-phenylpropylamine, under the process conditions described above for the preparation of 3-ATM HCl.

These three impurities are identified through separate syntheses, wherein (±)TMX is purposely prepared from 2FT (2-fluorotoluene) containing known amounts of 3FT (3-fluorotoluene), 4FT (4-fluorotoluene), and FB (fluorobenzene), in an amount of about 2 percent by weight each. Relative amounts of the corresponding by-products formed in the reaction, as measured by GC, area percent, are in agreement with the expected aromatic activation towards nucleophilic displacement. That is, the amount of D-ATM HCl from FB is greater than the amount of 3-ATM HCl from 3FT, which is greater than the amount of 4-ATM HCl from 4FT. The relative amounts of the impurities found in excess of the 2FT recovered after reaction are also in agreement. That is, the amount of FB is less than the amount of 3FT, which is less than the amount of 4FT. The results are provided in Table 1

TABLE 1

| SAMPLE | FB | 2FT | 3FT | 4FT |
|---|---|---|---|---|
| Starting 2FT composition: | 1.46% | 94.30% | 2.12% | 1.98% |
| Distillate (containing excess 2FT and impurities) | 0.56% | 95.45% | 1.18% | 2.19% |
| | D-ATM | ATM | 3-ATM | 4-ATM |
| TMX base end of reaction | 5.97% | 88.07% | 4.41% | 1.35% |
| Purification factor from 2-FT to TMX base end of reaction | 0.24 | 1.07 | 0.48 | 1.47 |

The (±)Tomoxetine solution from the stepwise process for the synthesis of ATM hydrochloride and the intermediates are analyzed by gas chromatography to separate the three impurities from the ATM, which, being GC achiral, always produces peaks including both enantiomers.

In a purification process, given an analytical technique producing peaks corresponding to impurities in samples, a purification factor of impurity X can be defined as follows:

(peak area % of X in starting material sample)/(peak area % of X in product sample)

This calculation implies that the higher the purification factor, the easier the removal of the impurity, and that purification factors below 1 indicate that it is likely to be extremely difficult, if not impossible, to remove the impurity.

Very low purification factors are generally obtained for the 3-ATM, 4-ATM, and D-ATM impurities, which had a maximum value of 4.56. Values of greater than 50 are found for other impurities, and the removal of those impurities is found to be effective. Purification factors of less than 1 are also found for the D-ATM impurity in the Mandelate salt stage. A detailed analysis is provided in the following tables, where GC area percent data are reported together with calculated purification factors, i.e., the ratio of A % for the starting material to A % for the product, for each impurity in each step in the synthesis.

TABLE 2

Step 2: Crude Atomoxetine (S)-(+) mandelate salt (crude ATM-SMA) formation

| Impurity | (±)TMX solution (A%) | Crude ATM-SMA (A%) | Purification Factor |
|---|---|---|---|
| D-ATM-SMA | 5.97 | 7.33 | 0.81 |
| ATM-SMA | 88.07 | 88.30 | 1.00 |
| 3-ATM-SMA | 4.41 | 3.13 | 1.41 |
| 4-ATM-SMA | 1.35 | 1.21 | 1.12 |

TABLE 3

Step 3: Purified Atomoxetine (S)-(+) mandelate salt (purified ATM-SMA) formation

| Impurity | Crude ATM-SMA (A%) | Purified ATM-SMA (A%) | Purification Factor |
|---|---|---|---|
| D-ATM-SMA | 7.33 | 8.34 | 0.88 |
| ATM-SMA | 88.30 | 88.32 | 1.00 |
| 3-ATM-SMA | 3.13 | 2.28 | 1.37 |
| 4-ATM-SMA | 1.21 | 1.05 | 1.15 |

TABLE 4

Steps 4 and 5: Atomoxetine Hydrochloride (ATM HCl) formation

| Impurity | Purified ATM-SMA (A%) | ATM HCl (A%) | Purification Factor |
|---|---|---|---|
| D-ATM | 8.34 | 3.70 | 2.25 |
| ATM | 88.32 | 95.60 | 0.92 |
| 3-ATM | 2.28 | 0.50 | 4.56 |
| 4-ATM | 1.05 | 0.30 | 3.50 |

The purification factors calculated for the final amounts of D-ATM HCl, 3-ATM HCL, and 4-ATM HCL may be used to back-calculate the amounts of FB, 3FT and 4FT in the 2-fluorotoluene starting material. The calculation is as follows:

| | | | |
|---|---|---|---|
| Final: | D-ATM HCl | 3-ATM HCl | 4-ATM HCl |
| GC A% | 0.15 | 0.15 | 0.15 |
| Purified intermediate: | pD-ATM-SMA | p3-ATM-SMA | p4-ATM-SMA |
| GC A% | 0.34 | 0.68 | 0.53 |
| Crude intermediate: | cD-ATM-SMA | c3-ATM-SMA | c4-ATM-SMA |
| GC A% | 0.30 | 0.94 | 0.61 |
| (±)TMX: | (±) D-TMX | (±) 3-TMX | (±) 4-TMX |
| GC A% | 0.24 | 1.32 | 0.68 |
| Corresponding 2FT starting material: | FB | 3FT | 4FT |
| GC A% | 0.059 | 0.636 | 0.990 |

Despite a process that includes five purification steps, i.e., two extractions and three crystallizations, the removal of 3-ATM HCl, 4-ATM HCl and D-ATM HCl is surprisingly low. Therefore, Atomoxetine Hydrochloride of the desired purity is typically not obtained, as commonly expected, by the repetition of purification steps used typically in the art. The desired purity may be obtained by limiting the amounts of the impurities 3FT, 4FT, and FB in the 2-fluorotoluene starting material. The limit amounts of the 3FT, 4FT, and FB impurities may be defined through the purification factor calculations described above, only if a suitable reference standard is available.

The present invention provides various methods involving the use of 3-ATM HCl, 4-ATM HCl, and D-ATM HCl as reference markers or reference standards.

When using these impurities enantiomerically pure, they will be eluted at the same retention time as their racemates.

Provided is a method of identifying an impurity in a sample of Atomoxetine Hydrochloride comprising:

(a) providing a reference sample comprising a reference marker and Atomoxetine Hydrochloride;

(b) carrying out HPLC or GC on the reference sample to determine the relative retention time of the reference marker compared to Atomoxetine hydrochloride;

(c) carrying out HPLC or GC on the sample of Atomoxetine hydrochloride to determine the relative retention time of the impurity compared to Atomoxetine hydrochloride;

(d) comparing the relative retention times determined in steps (b) and (c);

where, if the relative retention times determined in steps (b) and (c) are substantially the same, the impurity is identified as being the same as the reference marker;

where the reference marker is selected from the group consisting of 3-ATM HCl, 4-ATM HCl and D-ATM HCl.

Also provided is a method of determining the amount of an impurity in a sample of atomoxetine hydrochloride comprising:

(a) adding a known amount of a reference standard to the atomoxetine hydrochloride sample;

(b) subjecting the atomoxetine hydrochloride to HPLC or GC;

(c) identifying and measuring the area of an HPLC or GC peak associated with the impurity;

(d) identifying and measuring the area of an HPLC or GC peak associated with the reference standard;

(e) calculating the amount of the impurity in the atomoxetine hydrochloride sample based on the results of steps (c) and (d);

where the reference standard is selected from the group consisting of 3-ATM HCl, 4-ATM HCl and D-ATM HCl.

Also provided is a method of determining the amount of an impurity in a sample of atomoxetine hydrochloride comprising:

(a) providing a sample of atomoxetine hydrochloride containing an unknown concentration of the impurity;

(b) providing a sample of a known concentration of the impurity;

(c) subjecting a portion of the sample of atomoxetine hydrochloride and a portion of the sample of the impurity to HPLC or GC;

(d) measuring the area of the impurity peaks obtained from the sample of atomoxetine hydrochloride and from the sample of the impurity; and (e) calculating the concentration of the impurity in the sample of Atomoxetine Hydrochloride from the measurements of step (d);

where the impurity is selected from the group consisting of 3-ATM HCl, 4-ATM HCl and D-ATM HCl.

Also provided is a method of ensuring the purity of a preparation of Atomoxetine Hydrochloride comprising:

(a) choosing a predetermined level of the impurities 3-ATM HCl, 4-ATM HCl and D-ATM HCl.

(b) measuring the purification factor for each impurity formed during each step of the method of synthesizing Atomoxetine Hydrochloride;

(c) calculating the highest level of 3-fluorotoluene, 4-fluorotoluene, and fluorobenzene that may be present in the 2-fluorotoluene such that the levels of 3-ATM HCl, 4-ATM HCl and D-ATM HCl in the Atomoxetine Hydrochloride produced are below the predetermined levels;

where step (c) involves the use of 3-ATM HCl, 4-ATM HCl and D-ATM HCl as reference standards.

Suitable methods of synthesizing Atomoxetine Hydrochloride that involve reacting 2-fluorotoluene with N-methyl-3-hydroxy-3-phenylpropylamine are known in the art and include those disclosed in European Patent Publication No. EP 0 052 492, U.S. Pat. Nos. 4,868,344 and 6,541,668 and International Patent Application Publication No. WO 00/58262. Typically, the synthetic path for the production of Atomoxetine comprises:

I. Tomoxetine synthesis, using 2-fluorotoluene as a reactant;

II. Tomoxetine optical resolution using (S)-(+)-Mandelic acid as a resolving agent; and III. Atomoxetine Hydrochloride formation and isolation.

Analytical Methods

Atomoxetine Hydrochloride impurities may be determined using the following gas chromatography apparatus and procedures:

| Column & Packing: | HP-35: 35% Phenyl Methyl Siloxane (Hewlett Packard cat. N° 19091G-113) or equivalent Length: 30 m Diameter: 0.32 mm Film thickness: 0.25 μm | |
|---|---|---|
| Injector temperature: | 250° C. | |
| Detector temperature: | 250° C. | |
| Oven temperature: | Time (min) | Temperature |
| | 0 | 180° C. |
| | 20.0 | 180° C. |
| | 23.5 | 250° C. |
| | 33.5 | 250° C. |
| Equilibrium time: | 5 min | |
| Injection volume: | 1 μl | |
| Carrier gas: | Nitrogen | |
| Flow: | 1.5 ml/min. | |
| Detector: | FID | |
| Split ratio: | 10/1 | |

Typical retention times that may be obtained are as follows:

| | RT | RRT |
|---|---|---|
| (±)D-ATM | 12.8' | 0.81 |
| ATM | 15.9' | 1.00 |
| (±)3-ATM | 16.9' | 1.06 |
| (±)4-ATM | 18.3' | 1.15 |

A sample chromatogram is shown in FIG. 1.

Sample solutions may be prepared as follows: About 15 mg of ATM HCl is dissolved in 1 ml of water. Then, 10 ml of n-hexane and 2 ml of a 5 percent by volume ammonia solution are added. The sample is mixed vigorously, and, after phase separation, about 1 ml of the upper organic phase is transferred into an injection vial.

2-fluorotoluene impurities may be determined using the following gas chromatography apparatus and procedures:

| Column & Packing: | Zebron ZB-WAX 100% Polyethylene glycol (Phenomenex cat. N° 7KK-G007-22) or equivalent Length: 60 m Diameter: 0.53 mm Film thickness: 1.0 μm | | |
|---|---|---|---|
| Injector temperature: | 180° C. | | |
| Detector temperature: | 200° C. | | |
| Oven temperature: | Rate ° C./min | Temperature | Hold min. |
| | | 60° C. | 24 |
| | 10.0 | 200° C. | 10 |
| Equilibrium time: | 3 min | | |
| Injection volume: | 1 μl | | |
| Carrier gas: | Nitrogen | | |
| Flow: | 3.0 ml/min. | | |
| Detector: | FID | | |
| Split ratio: | 10/1 | | |

Typical retention times that may be obtained are as follows:

| | RT | RRT |
|---|---|---|
| F-Benzene | 14.4' | 0.65 |
| 2-Butanol | 16.1' | 0.73 |
| 2-F Toluene | 22.1' | 1.00 |
| 3-F Toluene | 22.9' | 1.04 |
| 4-F Toluene | 23.5' | 1.06 |

Figure 2:
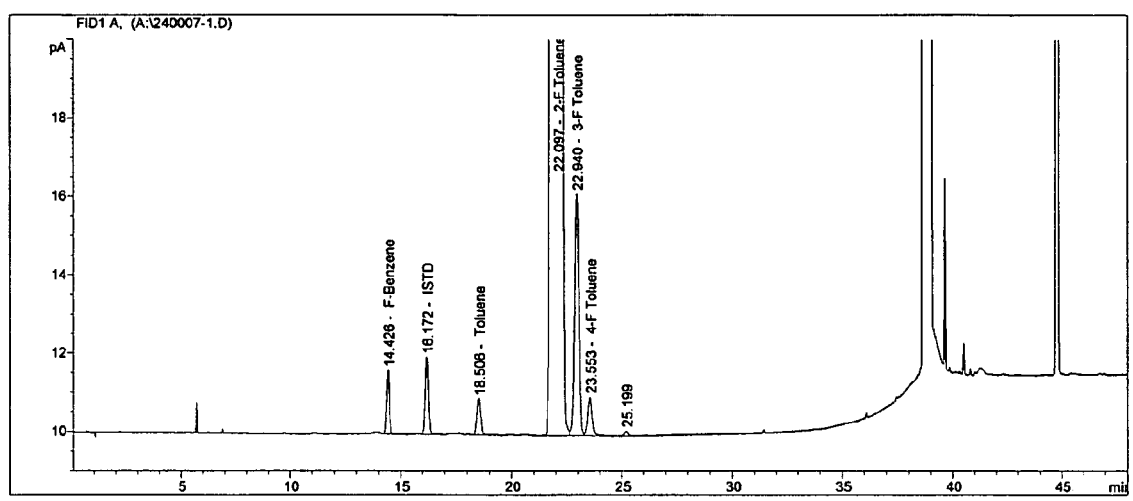
FIG. 2 shows a typical chromatogram of 2-fluorotoluene impurities obtained via GC on a Zebron ZB-WAX 100% Polyethylene glycol (Phenomenex cat. No 7KK-G007-22) column.

A sample chromatogram is shown in FIG. 2.

Quantitative analysis of atomoxetine may be performed using the following achiral HPLC method:

| Column & Packing: | YMC-Pack ODS-AQ, S-5 μm, 12 nm 250 mm × 4.6 mm × 5.0 μm, cat n.042574458 (W) or equivalent | | |
|---|---|---|---|
| Buffer: | NaH$_2$PO$_4$ monohydrate pH 3.0: 2.8 g in 1000 mL of deionized water, adjust pH at 3.0 with H$_3$PO$_4$ 85% (w/w). Filter on a 0.45 μm filter. | | |
| Eluent A: | Acetonitrile:Water 90:10 | | |
| Gradient | Time (min) | % Buffer | % Eluent A |
| | 0 | 85 | 15 |
| | 20 | 48 | 52 |
| | 30 | 48 | 52 |
| Equilibrium time: | 8 minutes | | |
| Flow Rate: | 1.5 mL/mins. | | |
| Detector: | UV at 215 nm | | |
| Column temperature: | 40° C. | | |
| Diluent | Buffer:Acetonitrile (60:40) | | |
| Injection | 5 μL | | |

Standard Solution Preparation:

Weigh accurately about 20 mg of Desmethylatomoxetine (D-ATM) standard into a 100 ml volumetric flask and dilute to volume with diluent solution. Transfer 0.5 ml of the obtained solution into 100 ml volumetric flask and dilute to volume with diluent solution.

Sample Solution Preparation:

Prepare a solution of about 1.0 mg/ml solution of ATM*HCl sample in diluent.

Procedure:

Inject blank run of diluent in order to get a good column stabilization and recognize the system peaks, 3 blank runs are suggested.

Inject standard and sample solution into chromatograph continuing the chromatogram of samples up to the end of gradient program.

Figure 3:
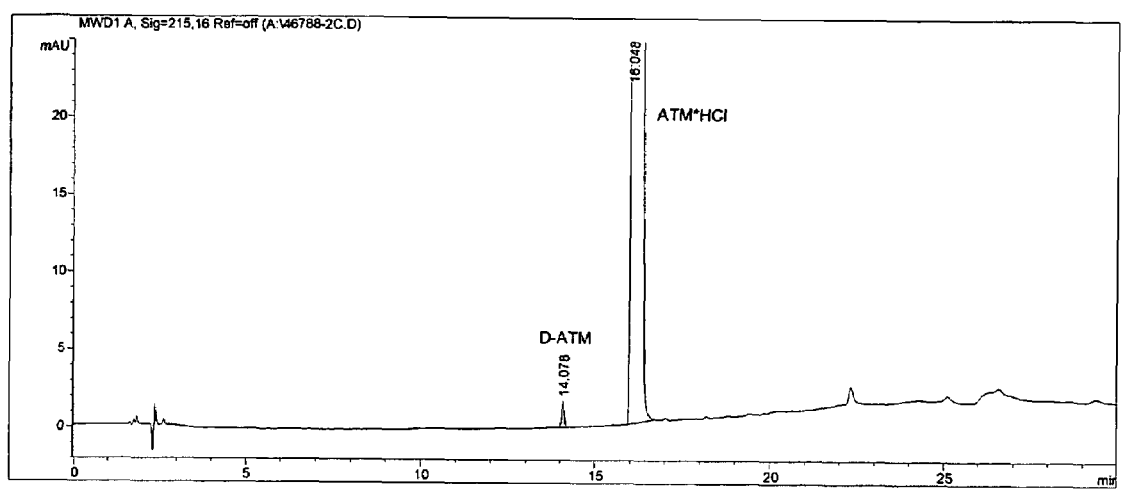
FIG. 3 shows a typical chromatogram of D-ATM obtained via achiral chromatography on a YMC-Pack ODS-AQ, S-5 μm column.

A sample chromatogram is shown in FIG. 3.

Enantiomeric purity can be established by the following chiral HPLC method:

| | |
|---|---|
| Column & Packing: | CHIRALCEL OD-R cellulose tris(3,5-dimethyl-phenylcarbamate) 250 mm × 4.60 mm × 10 um (Daicel chemicals cat. N˚ DAIC14625) or equivalent |
| Mobile phase: | KPF$_6$ 100 mM/ACN - 60/40 |
| Note: | continue the chromatogram up to 30 minutes |
| Sample volume: | 5.0 μL |
| Flow Rate: | 0.8 mL/min. |
| Detector: | UV at 215 nm |
| Column temperature: | 35° C. |
| Diluent | mobile phase |

Mobile phase composition and flow rate may be varied in order to achieve the required system suitability.

Figure 4:
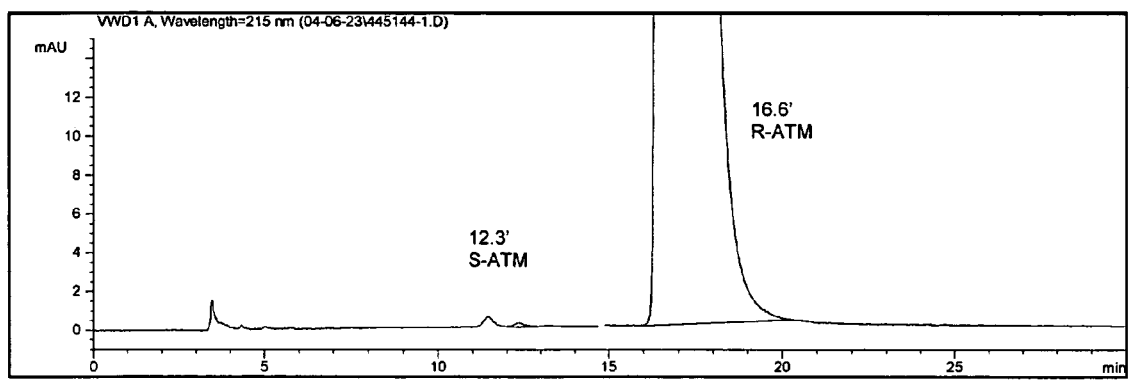
FIG. 4 shows a typical chromatogram of atomoxetine HCl obtained via chiral chromatography on a CHIRALCEL OD-R cellulose tris(3,5-dimethylphenylcarbamate) column.

A sample chromatogram is shown in FIG. 4.

EXAMPLES

While the present invention is described with respect to particular examples and preferred embodiments, it is understood that the present invention is not limited to these examples and embodiments. The present invention, therefore, includes variations from the particular examples and preferred embodiments described herein, as will be apparent to one of skill in the art.

Example 1

Synthesis of N-methyl-3-(3-methylphenoxy)-3-phenylpropylamine (3-ATM HCl)

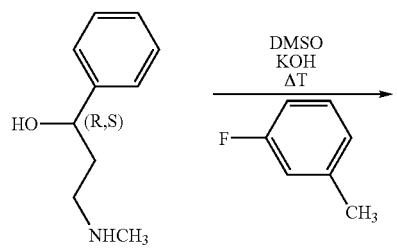

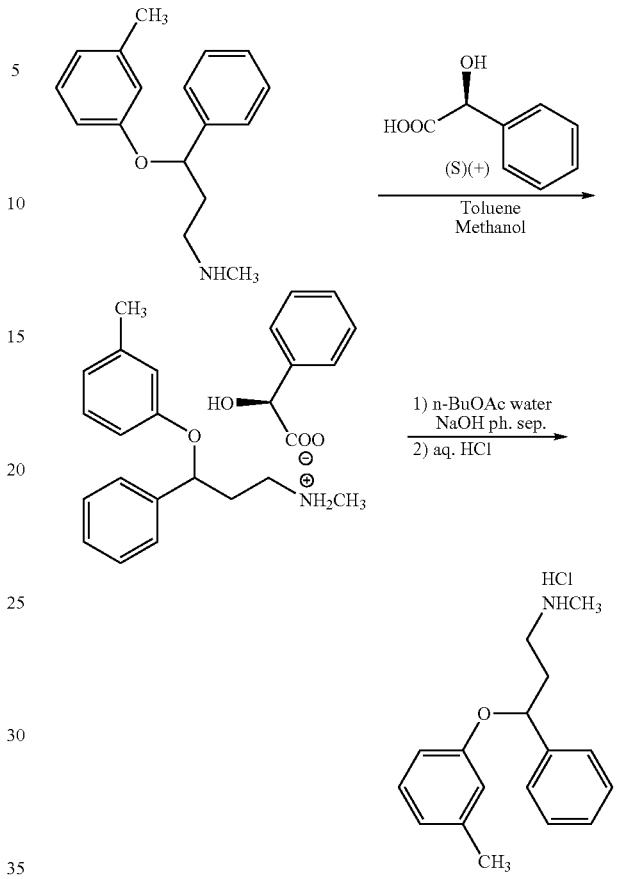

76 g (0.969 mol) of dimethylsulfoxide, 40 g (0.242 mol) of N-methyl-3-hydroxy-3-phenylpropylamine (100%, mw 165.12), and 75.5 g (1.211 mol) of potassium hydroxide (bulk industrial grade, 90% assay) are heated under stirring at 100° C. ±3° C. for 1 hour. The resulting mixture is cooled to 80° C., and, with good stirring, 79.95 g (0.726 mol) of 3-fluorotoluene are added over a period of about 1 hour, maintaining the temperature at 83° C. +3° C., resulting in the precipitation of salts. The mixture is then stirred at 83° C. ±3° C. for about 5 hours, and 300 ml of water and 300 ml of toluene are added. The mixture is stirred for a few minutes, and the phases are separated. The aqueous phase is extracted with 50 ml of toluene, and the organic phases are collected and washed three times with 80 ml of water. The washed organic phase is concentrated under vacuum at about 60° to about 80° C. to produce about 70 g of a liquid brown residue, which is crude (±)3-methyl Tomoxetine base (3-TMX) containing about 0.2 mol of 100% base. 400 ml of toluene, 3 ml of methanol, and 19.0 g (0.125 mol) of (S)-(+)-Mandelic acid are added at 25° C., producing a slurry that is heated to a temperature of from about 65° to about 70° C. until completely dissolved to form a solution. The resulting solution is then cooled to from about 5° to about 10° C., resulting in crystallization of solid 3-methyl Atomoxetine (S)-(+)-Mandelate salt (3-ATM-SMA), which is isolated by filtration, which is found to be difficult and slow, and washed with toluene, which also is found to be difficult and slow. After drying under vacuum at about 50° to about 60° C., 30 g of product are recovered.

The 30 g of dried 3-ATM-SMA are mixed under stirring with 150 ml of n-butyl acetate and 150 ml of water at room temperature. About 1 g of 30% aqueous sodium hydroxide are added to adjust the pH to about 12.5, and the phases are separated. The organic phase, containing 3-ATM base, is washed twice with 30 ml of water, filtered on paper, and used in the subsequent hydrochloride preparation as follows.

Under stirring, while maintaining the temperature between about 15° and about 25° C. with an ice-water bath, 8.55 g of 36% aqueous hydrogen chloride are dropped on the filtered organic phase, resulting in the crystallization and suspension of the 3-ATM Hydrochloride (mw 291.82). The suspension is stirred at about 20° C. for 1 hour, the solid is collected by filtration, washed twice with 35 ml of n-butyl acetate, and dried for 18 hours under vacuum at about 50° to about 60° C., yielding about 19.6 g of product, having a melting point of about 159° to about 160° C., and $^1$H-NMR data of 9.58 ppm, bs, 2H, 7.35-7.20 ppm, m, 5H, 7.01 ppm, t, 1H; 6.68-6.65 ppm, m, 2H, 6.59 ppm, dd, 1H, 5.30 ppm, dd, 1H; 3.10 ppm, quint, 2H; 2.57 ppm, t, 3H, 2.41 ppm, m, 2H, 2.22 ppm, s, 3H. The yield is 28 percent by weight based on the starting N-methyl-3-hydroxy-3-phenylpropylamine. The 3-ATM HCl is determined to be a mixture of enantiomers, with relative ratio: 99/1 by chiral HPLC.

Example 2

Synthesis of N-methyl-3-(4-methylphenoxy)-3-phenylpropylamine (4-ATM)

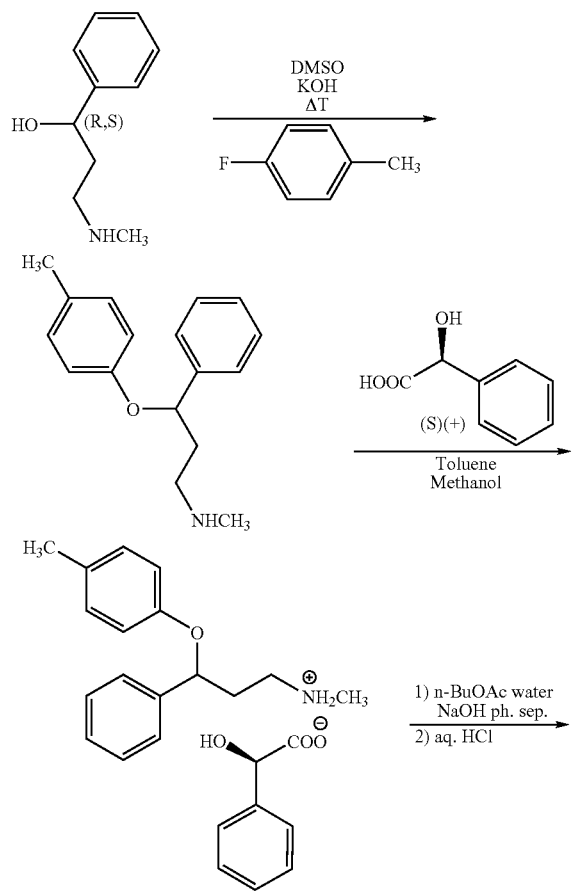

-continued

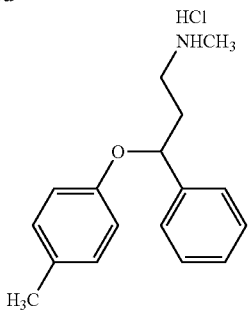

76 g (0.969 mol) of dimethylsulfoxide, 40 g (0.242 mol) of N-methyl-3-hydroxy-3-phenylpropylamine (100%, mw 165.12), and 75.5 g (1.211 mol) of potassium hydroxide (bulk industrial grade, 90% assay) are heated under stirring at 100° C. ±3° C. for 1 hour. The mixture is then cooled to from about 80° C., then, under good stirring, 79.95 g (0.726 mol) of 4-fluorotoluene are added in about 1 hour, maintaining the temperature at 83° C. ±3° C., resulting in the precipitation of salts. The mixture is then stirred at 83° C. ±3° C. for about 5 hours. 300 ml of water and 300 ml of toluene are then added, the mixture is stirred for a few minutes, and the phases are separated. The aqueous phase is extracted with 50 ml of toluene, and the organic phases are collected and washed with three times with 80 ml of water. The washed organic phase is concentrated under vacuum at about 60° to about 80° C., producing about 70 g of a liquid brown residue of crude (±)4-methyl Tomoxetine base (4-TMX) (about 0.2 mol of 100% base). 400 ml of toluene, 3 ml of methanol, and 19.0 g (0.125 mol) of (S)-(+)-Mandelic acid are added at 25° C., producing a slurry that is heated to a temperature of from about 65° to about 70° C. The resulting solution is then cooled to 0° C. for 2 hours. The solid 4-methyl Atomoxetine (S)-(+)-Mandelate salt (4-ATM-SMA) is isolated by filtration, washed with toluene, optionally washed with 40 ml of MTBE, and dried under vacuum at about 50° to about 60° C., yielding 50 g of product.

The 50 g of dried 4-ATM-SMA are mixed under stirring with 250 ml of n-butyl acetate and 250 ml of water at room temperature. About 21 g of 30 percent aqueous sodium hydroxide are added to adjust the pH to about 12.5, and the phases are separated. The organic phase, containing the 4-ATM base, is washed twice with 30 ml of water, filtered on paper, and used in subsequent hydrochloride preparation as follows.

Under stirring, while maintaining the temperature between about 15° and about 25° C. with an ice-water bath, 14.25 g of 36 percent aqueous hydrogen chloride are dropped on the filtered organic phase. 4-ATM Hydrochloride (mw 291.82) crystallizes in bulk, and 40 ml of n-butyl acetate are added to allow stirring. The resulting suspension is stirred at about 20° C. for 1 hour, the solid is collected by filtration, washed twice with 40 ml of n-butyl acetate, and dried for 18 hours under vacuum at about 50° to about 60° C., yielding 23.5 g of product, having a melting point of about 164° to about 167° C., for a 33 percent yield, based on the N-methyl-3-hydroxy-3-phenylpropylamine starting material. The 4-ATM HCl is found by chiral HPLC as a mixture of enantiomers, with a relative ratio of 58:42.

Example 3

Synthesis of N-methyl-3-phenoxy-3-phenylpropylamine (D-ATM)

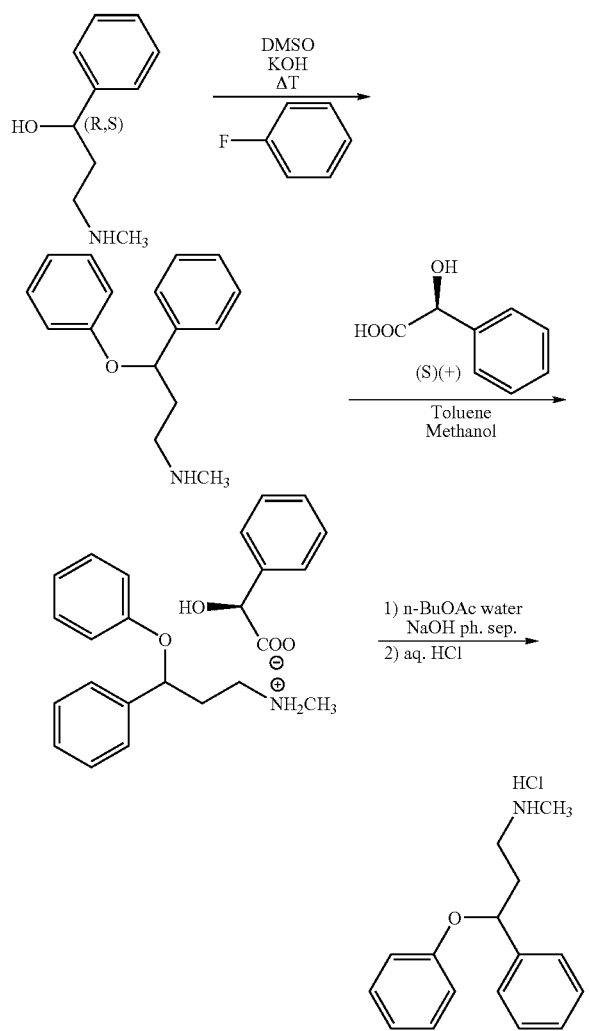

76 g (0.969 mol) of dimethylsulfoxide, 40 g (0.242 mol) of N-methyl-3-hydroxy-3-phenylpropylamine (100%, mw 165.12), and 75.5 g (1.211 mol) of potassium hydroxide (bulk industrial grade, 90% assay) are heated under stirring at 100° C. ±3° C. for 1 hour. The mixture is then cooled to 80° C., and, under good stirring, 69.77 g (0.726 mol) of fluorobenzene are added in about 1 hour, maintaining the temperature at 83° C. ±3° C., precipitating salts. The mixture is stirred at 83° C. ±3° C. for about 5 hours, 300 ml of water and 300 ml of toluene are added, and the mixture is stirred for a few minutes. The phases are then separated, and the aqueous phase is extracted with 50 ml of toluene. The organic phases are collected, and washed three times with 80 ml of water. The washed organic phase is concentrated under vacuum at about 60° to about 80° C., yielding about 70 g of liquid brown residue, i.e., crude (±) Desmethyl Tomoxetine base (D-TMX) (about 0.2 mol of 100% base).

400 ml of toluene, 3 ml of methanol, and 19.0 g (0.125 mol) of (S)-(+)-Mandelic acid are added at 25° C., producing a slurry that is heated to a temperature of from about 65° to about 70° C. (incomplete solubilization), followed by cooling to from about 5° to about 10° C. Solid Desmethyl Atomoxetine (S)-(+)-Mandelate salt (D-ATM-SMA) is isolated by filtration, washed with toluene, and dried under vacuum at about 50° to about 60° C., yielding 48 g of product. The 48 g of dried D-ATM-SMA are mixed under stirring with 250 ml of n-butyl acetate and 250 ml of water at room temperature. About 16 g of 30 percent aqueous sodium hydroxide are added to adjust the pH to about 12.5, and the phases are separated. The organic phase, containing D-ATM base, is washed twice with 35 ml of water, filtered on paper, and used in subsequent hydrochloride preparation as follows.

Under stirring, while maintaining the temperature between about 15° and about 25° C. with an ice-water bath, 12.3 g of 36 percent aqueous hydrogen chloride are dropped on the filtered organic phase, resulting in the crystallization of D-ATM hydrochloride (mw 277.80). The resulting suspension is stirred at about 20° C. for 1 hour, the solid is collected by filtration, washed twice with 40 ml of n-butyl acetate, and dried for 18 hours under vacuum at about 50° to about 60° C., yielding 32.7 g of product, a 48 percent yield based on the N-methyl-3-hydroxy-3-phenylpropylamine starting material, having a melting point of about 170° to about 174° C. The D-ATM HCl is found by chiral HPLC to be a mixture of enantiomers, with a relative ratio of 69:31.

What is claimed is:

1. Isolated N-methyl-3-(3-methylphenoxy)-3-phenylpropylamine hydrochloride.

2. A method of preparing N-methyl-3-(3-methylphenoxy)-3-phenylpropylamine hydrochloride (3-ATM HCl) comprising:
   (a) combining N-methyl-3-hydroxy-3-phenylpropylamine with DMSO in the presence of a strong base at a temperature of at least 90° C. to form a mixture;
   (b) adding 3-fluorotoluene to the mixture formed in (a), to form a reaction mixture, and maintaining the reaction mixture for at least 5 hours;
   (c) adding a first organic solvent and water to the reaction mixture;
   (d) recovering crude (±)3-methyl Tomoxetine base;
   (e) combining the crude (±)3-methyl Tomoxetine base with (S)-(+)-Mandelic acid in the presence of a $C_{1-4}$ alcohol and an aromatic solvent, and heating to a temperature of about 65° C. to about 70° C.;
   (f) recovering 3-methyl Atomoxetine (S)-(+)-Mandelate salt;
   (g) combining the recovered 3-methyl Atomoxetine (S)-(+)-Mandelate salt with a second organic solvent, water and a base;
   (h) recovering 3-methyl Atomoxetine base; and
   (i) converting the recovered 3-methyl Atomoxetine base into its hydrochloride salt.

3. The method of claim 2 where step (a) comprises combining about 0.1 to 20 moles of DMSO per mole of N-methyl-3-hydroxy-3-phenylpropylamine.

4. A method of preparing N-methyl-3-(4-methylphenoxy)-3-phenylpropylamine hydrochloride (4-ATM HCl) comprising:
   (a) combining N-methyl-3-hydroxy-3-phenylpropylamine with DMSO in the presence of a strong base at a temperature of at least 90° C. to form a mixture;
   (b) adding 4-fluorotoluene to the mixture formed in (a), to form a reaction mixture, and maintaining the reaction mixture for at least 5 hours;

(c) adding a first organic solvent and water to the reaction mixture;
(d) recovering crude (±) 4-methyl Tomoxetine base;
(e) combining the crude (±) 4-methyl Tomoxetine base with (S)-(+)-Mandelic acid in the presence of a $C_{1-4}$ alcohol and an aromatic solvent, and heating to a temperature of about 65° C. to about 70° C.;
(f) recovering 4-methyl Atomoxetine (S)-(+)-Mandelate salt;
(g) combining the recovered 4-methyl Atomoxetine (S)-(+)-Mandelate salt with a second organic solvent, water and a base;
(h) recovering 4-methyl Atomoxetine base; and
(i) converting the recovered 4-methyl Atomoxetine base into its hydrochloride salt.

5. The method of claim 4 where step (a) comprises combining about 0.1 to 20 moles of DMSO per mole of N-methyl-3-hydroxy-3-phenylpropylamine.

6. A method of preparing N-methyl-3-phenoxy-3-phenyl-propyl-amine hydrochloride (D-ATM HCl) comprising:
(a) combining N-methyl-3-hydroxy-3-phenylpropylamine with DMSO in the presence of a strong base at a temperature of at least 90° C. to form a mixture;
(b) adding fluorobenzene to the mixture formed in (a), to form a reaction mixture, and maintaining the reaction mixture for at least 5 hours;
(c) adding a first organic solvent and water to the reaction mixture;
(d) recovering crude (±) D-Tomoxetine base;
(e) combining crude (±) D-Tomoxetine base with (S)-(+)-Mandelic acid in the presence of a $C_{1-4}$ alcohol and an aromatic solvent, and heating to a temperature of about 65° C. to about 70° C.;
(f) recovering D-Atomoxetine (S)-(+)-Mandelate salt;
(g) combining the recovered D-Atomoxetine (S)-(+)-Mandelate salt with a second organic solvent, water and a base;
(h) recovering D-Atomoxetine base; and
(i) converting the recovered D-Atomoxetine base into its hydrochloride salt.

7. The method of claim 6 where step (a) comprises combining about 0.1 to 20 moles of DMSO per mole of N-methyl-3-hydroxy-3-phenylpropylamine.

8. The method of claim 2 where the strong base is KOH.

9. The method of claim 2 where the 3-fluorotoluene is added in step (b) in an amount of at least 2 moles per mole of N-methyl-3-hydroxy-3-phenylpropylamine.

10. The method of claim 2 where the first organic solvent in step c) is selected from the group consisting of toluene, benzene, xylenes, di-isopropyl ether, methyl-tert-butyl, ethyl acetate n-butylacetate, and isobutylacetate.

11. The method of claim 2 where the $C_{1-4}$ alcohol in step e) is methanol and is added in an amount of about 0.1 mL per 1 g of the (±)3-methyl Tomoxetine base.

12. The method of claim 4 where the strong base is KOH.

13. The method of claim 4 where the 4-fluorotoluene is added in step (b) in an amount of at least 2 moles per mole of N-methyl-3-hydroxy-3-phenyl-propylamine.

14. The method of claim 4 where the first organic solvent in step c) is selected from the group consisting of toluene, benzene, xylenes, di-isopropyl ether, methyl-tert-butyl, ethyl acetate n-butylacetate, and isobutylacetate.

15. The method of claim 4 where the $C_{1-4}$ alcohol in step e) is methanol and is added in an amount of about 0.1 mL per 1 g of the (±) 4-methyl Tomoxetine base.

16. The method of claim 6 where the strong base is KOH.

17. The method of claim 6 where the fluorobenzene is added in step (b) in an amount of at least 2 moles per mole of N-methyl-3-hydroxy-3-phenyl-propylamine.

18. The method of claim 6 where the first organic solvent in step c) is selected from the group consisting of toluene, benzene, xylenes, di-isopropyl ether, methyl-tert-butyl, ethyl acetate n-butylacetate, and isobutylacetate.

19. The method of claim 6 where the $C_{1-4}$ alcohol in step e) is methanol and is added in an amount of about 0.1 ml per 1 g of the (±) D-methyl Tomoxetine base.

* * * * *